(12) United States Patent
Craig

(10) Patent No.: US 6,200,763 B1
(45) Date of Patent: Mar. 13, 2001

(54) MYELOID CELL LEUKEMIA ASSOCIATED GENE MCL-1

(75) Inventor: Ruth W. Craig, Hanover, NH (US)

(73) Assignee: Dartmouth College, Hanover, NH (US)

( * ) Notice: Subject to any disclaimer, the term of this patent is extended or adjusted under 35 U.S.C. 154(b) by 0 days.

(21) Appl. No.: 09/378,536

(22) Filed: Aug. 20, 1999

Related U.S. Application Data

(62) Division of application No. 09/211,640, filed on Dec. 15, 1998, now Pat. No. 6,020,466, which is a division of application No. 08/441,375, filed on May 15, 1995, now Pat. No. 5,888,812, which is a division of application No. 08/077,848, filed on Jun. 16, 1993, now Pat. No. 5,470,955, which is a continuation-in-part of application No. 08/012,307, filed on Feb. 2, 1993, now abandoned.

(51) Int. Cl.⁷ .......................... G01N 33/53; C07K 16/00; C07K 1/00; C07K 14/00; C12P 21/08
(52) U.S. Cl. .......................... 435/7.1; 435/330; 435/344; 435/366; 530/386; 530/387.7; 530/388.1; 530/388.15
(58) Field of Search ................. 424/138.1, 141.1, 424/178.1, 183.1; 435/6, 69.1, 91.1, 91.31, 91.5, 91.51, 325, 375, 330; 514/44; 530/300, 324, 350, 387.1, 388.1

(56) References Cited

PUBLICATIONS

Branch, A. 1998 Trends in Biochem Sci. (TIBS) vol. 23, pp. 45–50.*
Crooke, S.T. 1998. Antisense Research & Application. Chapter 1, pp. 1–50. (Publisher Springer–Verlage).*

* cited by examiner

*Primary Examiner*—Remy Yucel
*Assistant Examiner*—Jane Zara
(74) *Attorney, Agent, or Firm*—Gary Cary Ware & Freidenrich LLP; Lisa A. Haile

(57) ABSTRACT

A gene, mcl-1, of the bcl-2 family is disclosed along with its nucleotide and amino acid sequence. Also disclosed are diagnostic and therapeutic methods of utilizing the mcl-1 nucleotide and polypeptide sequences.

8 Claims, 8 Drawing Sheets

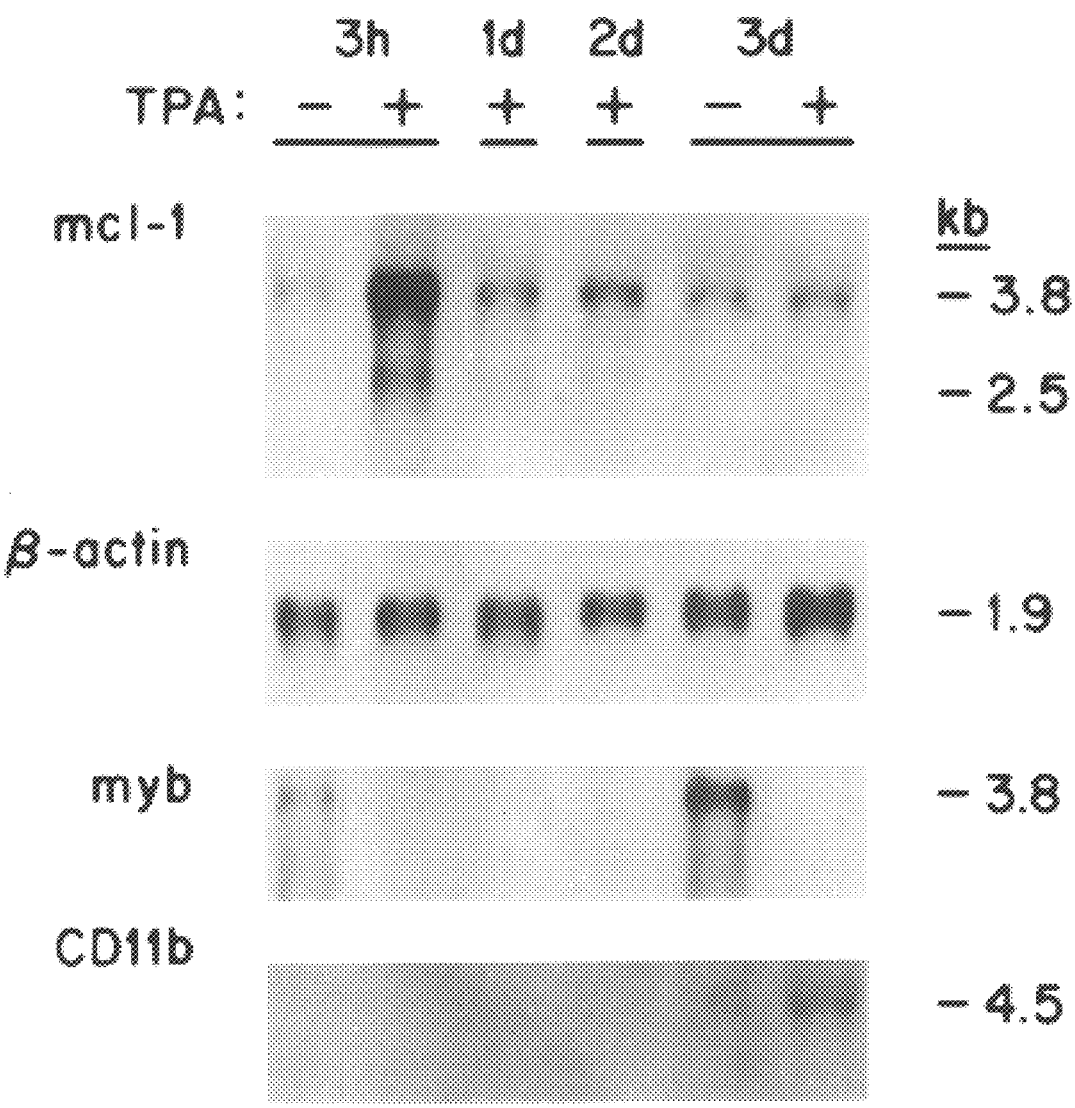
FIG. IA

```
  1  MFGLKRNAVIGLNLYCGGGAGLGAGSGGATRPGGRLLATEKEASARRREIGG        50
                                                  **
 51  GEAGAVIGGSAGASPPSTLTPDSRRVARPPPIGAEVPDVTATPARLLFFA         100
                          **
101  PTRRAAPLEEMEAPAADAIMSPEEELDGYEPEPLGKRPAVLPLLELVGES          150
         ***                      ++
151  GNNTSTDGSLPSTPPPAEEEEDELYRQSLEIISRYLREQATGAKDTKPMG          200
                               +
                   V
201  RSGATSRKALETLRRVGDGVQRNHETFQGMLRKLDIKNEDDVKSLSRVM           250
              -->**        A
251  IHVFSDGVTNWGRIVTLISFGAFVAKHLKTINQESCIEPLAESITDVLVR          300

301  TKRDWLVKQRGWDGFVEFFHVEDLEGGIRNVLLAFAGVAGVGAGLAYLIR          350
                              +
```

FIG. 2A

```
Consensus (mcl-1/bcl-2)            TLR  GD   R    F  M  Li       h   a  vi
                                                       v
mcl-1         212  TLRRVGDGVQRNHETAPQGMLRKLDIKN-EDD-VKSLSRVMIH
                   ||:.|:::::  ::     :: ::: ::    :   :
bcl-2alpha     86  LSPVPPVV---HLTLRQAGDDFSRRYRRDFAEMSRQLHLTPFTAR-GR-FATVEE
                   ||:.|                   :::::.|::  :::::
BHRF-1         40  LSPEDTVVLRYHVLL-----EEIIERNSETFTETWNRF-ITH-TEHVDLDFNSVFLE Consensus           iF DGV NWGRIVa  FGa i          i aiN E S       id iA    iTd L R   h
                    ***********  **
mcl-1              VFSDGVTNWGRIVTLISFGAFV--AKHLKTINQE-SC---IEPLAES-ITDVLVRTKR
                   ::||:|:|||||:    ::     :              :::     ::: :::
bcl-2alpha         LFRDGV-NWGRIVAFFEFGGVM---C---VESVNREMSP--LVDNIALW-MTEYLNRHLH
                   ::: ::  |:|::    ::::   :   : : :  :  :::::
BHRF-1             IFHRGDPSLGRALAWMAW---CMHACRTL-CCNQS-TPYYVVD-LSVRGMLE-ASEGLD Consensus          Wi   d GWDaFVE f          h iD     aih i L La  G A ia G AYL h
                   ************                               +                  +
mcl-1              DWLVKQRGWDGFVEFF-----H-VEDLE-G-GIRNV-L-LAFAGVGVGAGLAYLIR-
                   :| ::  |||:|||         ::.::           :||:|:  ::::|::
bcl-2alpha         TWIQDNGGWDAFVELYGP-SMRPLFDFSW-LSLKTL-LSLALVG-ACITLG-AYLGHK
                   .|: :: ||| ||:                :   :    ::|  ||: :::|: :
BHRF-1             GWIHQQGGWSTLIEDNIPGSRR----FSWTLFLAGLTLSL-LVI--CSYL-FISRGRH
```

MYELOID CELL LEUKEMIA ASSOCIATED GENE MCL-1

This is a request for filing a divisional application of prior application Ser. No. 09/211,640, filed on Dec. 15, 1998, U.S. Pat. No. 6,020,466, which is a division of application Ser. No. 08/441,375, filed on May 15, 1995, now U.S. Pat. No. 5,888,812, which is a division of application Ser. No. 08/077,848, filed on Jun. 16, 1993 and issued into U.S. Pat. No. 5,470,955, which is a continuation-in-part application of Ser. No. 08/012,307, filed Feb. 2, 1993, abandoned.

This invention was made with Government support under Grant No. CA54385 awarded by the National Institutes of Health. The Government has certain rights in this invention.

BACKGROUND OF THE INVENTION

1. Field of the Invention

The present invention relates generally to unique proto-oncogene polypeptides and specifically to a novel polypeptide of the bcl-2 family and its nucleic acid sequence.

2. Description of the Related Art

Advances in recombinant DNA technology have led to the discovery of normal cellular genes (proto-oncogenes and tumor suppressor genes, and apoptosis/cell death-related genes) which control growth, development, and differentiation. Under certain circumstances, regulation of these genes is altered and normal cells assume neoplastic growth behavior. In some cases, the normal cell phenotype can be restored by various manipulations associated with these genes. There are over 40 known proto-oncogenes and suppressor genes to date, which fall into various categories depending on their functional characteristics. These include, 1) growth factors and growth factor receptors, 2) messengers of intracellular signal transduction pathways, for example, between the cytoplasm and the nucleus, and 3) regulatory proteins influencing gene expression and DNA replication.

Qualitative changes in the structure of proto-oncogenes or their products and quantitative changes in their expression have been documented for several cancers. With chronic myelogenous leukemia, for example, the abl oncogene is translocated to chromosome 22 in the vicinity of the bcr gene. A cancer specific fusion protein, qualitatively different from parent cell proteins, is produced and is an ideal cancer marker. Mutant ras genes have been implicated in the earliest stages of human leukemias and colon cancers. The detection of these mutations in defined premalignant states could provide valuable prognostic information for clinicians.

During their life span, cells normally pass from an immature state with proliferative potential, through sequential stages of differentiation, to eventual cell death. This orderly progression is aberrant in cancer, probably due to alterations in oncogenes, tumor suppressor genes, and other genes. The progression from the immature state to differentiation can be reestablished in inducible leukemia cell lines. For example, ML-1 human myeloblastic leukemia cells can be induced to differentiate to monocytes/macrophages with the phorbol ester, 12-O-tetradecanoylphorbol-13-acetate (TPA). The differentiated cells lose proliferative capacity and accumulate in the $G_0/G_1$ phase of the cell cycle, while remaining viable and capable of carrying out normal monocyte/macrophage functions. In general, immature, proliferative cells convert to a differentiated, viable, non-proliferative phenotype.

In ML-1 cells, the initial induction of "programming" of this conversion can be separated from the subsequent phenotypic changes. When cells are induced with TPA for three hours under specific conditions, they become irreversibly committed to undergo differentiation over the next three days. This temporal separation can be used to identify genes that increase in expression during the early programming of differentiation. Such "early-induction" genes might influence or help bring about the later phenotypic conversion. Aberrant expression of these early-induction genes, such as the proto-oncogene fos, may lead to development of a transformed phenotype.

Research on oncogenes and their products is motivated partly by the belief that a more fundamental understanding of the mechanisms of cancer causation and maintenance will lead to more rational means of diagnosing and treating malignancies. Using family studies of restriction fragment length polymorphisms (RFLPs) genetically linked to proto-oncogenes, it may be possible to identify cancer-prone individuals.

Current cancer tests are nonspecific and of limited clinical application. For example, a biochemical test, widely used for both diagnostic and monitoring of cancer, measures level of carcinoembryonic antigen (CEA). CEA is an oncofetal antigen detectable in large amounts in embryonal tissue, but in small amounts in normal adult tissues. Serum of patients with certain gastrointestinal cancers contains elevated CEA levels that can be measured by immunological methods. The amount of CEA in serum correlates with the remission or relapse of these tumors, with the levels decreasing abruptly after surgical removal of the tumor. The return of elevated CEA levels signifies a return of malignant cells. CEA, however, is also a normal glycoprotein found at low levels in nearly all adults. Moreover, this protein can be elevated with several nonmalignant conditions and is not elevated in the presence of many cancers. Therefore, it is far from ideal as a cancer marker.

A similar oncofetal tumor marker is alpha-fetoprotein, an embryonic form of albumin. Again, the antigen is detectable in high amounts in embryonal tissue and in low amounts in normal adults. It is elevated in a number of gastrointestinal malignancies including hepatoma. Like CEA, a decrease correlates with the remission of cancer and a re-elevation with relapse. There is insufficient sensitivity and specificity to make this marker useful for screening for malignancy or for monitoring previously diagnosed cancer in any but a few selected cases.

For years, various therapeutic agents have been used to alter the expression of genes or the translation of their messages into protein products. However, a major problem with these agents is that they tend to act indiscriminately such that healthy cells as well as malignant cells are affected. As a consequence existing chemotherapeutic regimes are often associated with severe side effects due to the non-specific activity of these agents.

One possible approach to specific intentional therapy is by targeting cells expressing particular oncogenes, tumor suppressor genes or apoptosis/cell death genes. Therefore, there is a continual need to identify new oncogenes associated with cancer and neoplastic phenotypes and with the suppression of these phenotypes. Once these genes are identified, specific therapeutics may be designed which are directed, for example, against the genes themselves, their RNA transcripts or their protein products which should have minimal detrimental effect on healthy cells.

SUMMARY OF THE INVENTION

The present invention arose from the seminal discovery of a new gene, mcl-1, which is associated with certain cell proliferative disorders. This new gene was initially identified based on expression during the programming of differentiation in myeloid cell leukemia. As a result of this pioneering discovery, the present invention provides at its most fundamental level, a functional polypeptide, mcl-1, and the polynucleotide which encodes mcl-1. The novel polypeptide allows the production of antibodies which are immunoreactive with all or a portion of mcl-1, which can be utilized in various diagnostic and therapeutic modalities to detect and treat cell proliferative disorders associated with mcl-1.

BRIEF DESCRIPTION OF THE DRAWINGS

FIGS. 1A–C show a time course of expression of mcl-1 during the TPA-induced differentiation of ML-1 cells.

FIG. 2A–B show the deduced amino acid sequence of the mcl-1 protein and schematic representation of the cDNA.

FIG. 4 shows the amino acid alignment of the carboxyl regions of mcl-1, bcl-2, and BHRF1.

FIGS. 5A–5B are the nucleotide sequence of mcl-1.

DETAILED DESCRIPTION OF THE INVENTION

Figure 1B:
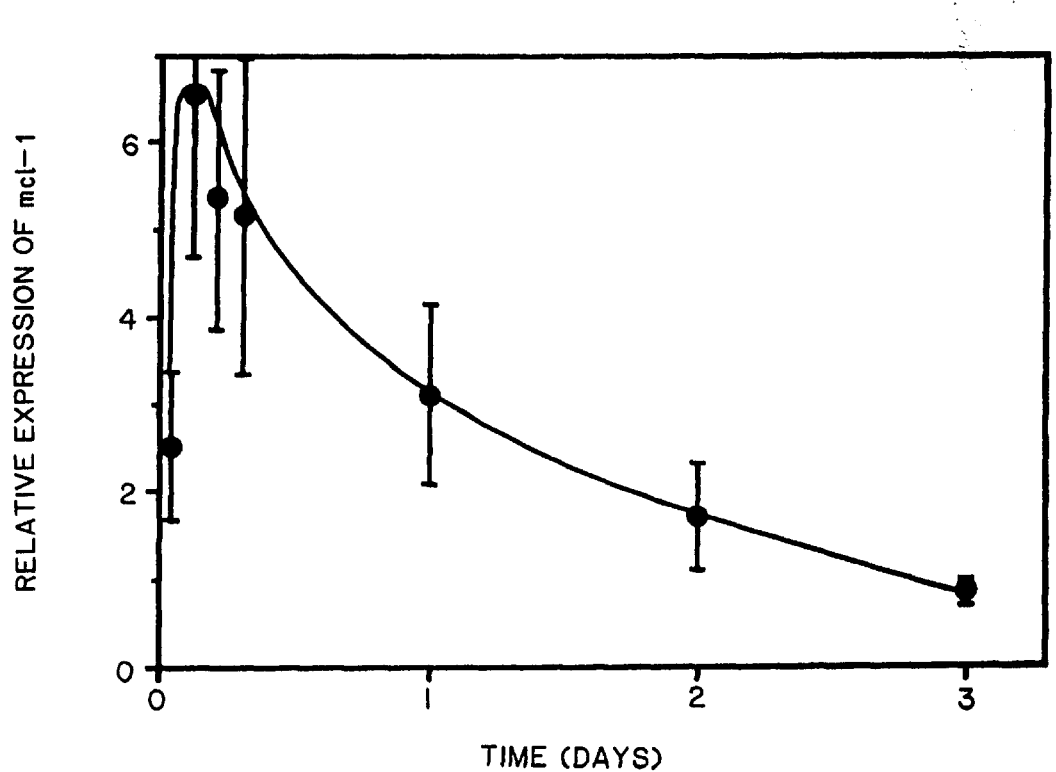

The present invention provides a novel polypeptide, mcl-1, which is expressed early during the programming of differentiation of myeloid cell leukemia. Genes expressed early in cell differentiation may participate in the induction or programming of the ensuing phenotypic changes. Also included is the polynucleotide sequence which encodes mcl-1 or portions thereof. The carboxyl portion of mcl-1 has homology to bcl-2, which inhibits programmed cell death in developing lymphoid cells and lymphoma. The mcl-1/bcl-2 family of genes are identified in cancer cells, but are distinct from known oncogenes in that they are characterized by an association with the programming of transitions in cell fate, such as from viability to death or from proliferation to differentiation. The invention provides a 3946 base pair polynucleotide which encodes a 37.5 kD polypeptide of the bcl-2 family. The invention also includes antibodies immunoreactive with mcl-1 polypeptide or fragments of the polypeptide. The invention also provides a method for identifying a cell expressing mcl-1 and a method for treating an mcl-1 associated disorder.

As used herein, the term "functional polypeptide" refers to a polypeptide which possesses a biological function or activity which is identified through a defined functional assay and which is associated with a particular biologic, morphologic or phenotypic alteration in the cell. The biological function can vary from a polypeptide fragment as small as an epitope to which an antibody molecule can bind to as large as a polypeptide which is capable of participating in the characteristic induction or programming of phenotypic changes within a cell. A "functional polynucleotide" denotes a polynucleotide which encodes a functional polypeptide as described herein.

The term "substantially pure" means any mcl-1 polypeptide of the present invention, or any gene encoding an mcl-1 polypeptide, which is essentially free of other polypeptides or genes, respectively, or of other contaminants with which it might normally be found in nature, and as such exists in a form not found in nature. By "functional derivative" is meant the "fragments," "variants," "analogues," or "chemical derivatives" of a molecule. A "fragment" of a molecule, such as any of the DNA sequences of the present invention, includes any nucleotide subset of the molecule. A "variant" of such molecule refers to a naturally occurring molecule substantially similar to either the entire molecule, or a fragment thereof. An "analog" of a molecule refers to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th ed., Mack Publishing Co., Easton, Pa. (1980).

Similarly, a "functional derivative" of a gene encoding mcl-1 polypeptide of the present invention includes "fragments," "variants", or "analogues" of the gene, which may be "substantially similar" in nucleotide sequence, and which encode a molecule possessing similar activity to mcl-1 peptide.

Thus, as used herein, mcl-1 polypeptide includes any functional derivative, fragments, variants, analogues, chemical derivatives which may be substantially similar to the mcl-1 polypeptide described herein and which possess similar activity.

Minor modifications of the mcl-1 primary amino acid sequence may result in proteins which have substantially equivalent activity as compared to the mcl-1 polypeptide described herein. Such modifications may be deliberate, as by site-directed mutagenesis, or may a spontaneous. All of the polypeptides produced by these modifications are included herein as long as the biological activity of mcl-1 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which may not be required for mcl-1 biological activity.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Peptides of the invention can be synthesized by the well known solid phase peptide synthesis methods described Merrifield, *J. Am. Chem. Soc.,* 85:2149, 1962), and Stewart and Young, *Solid Phase Peptides Synthesis,* (Freeman, San Francisco, 1969, pp. 27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

As used herein, the terms "polynucleotide" or "mcl-1 polynucleotide" denotes DNA, cDNA and RNA which encode mcl-1 polypeptide as well as untranslated sequences which flank the structural gene encoding mcl-1. It is understood that all polynucleotides encoding all or a portion of mcl-1 polypeptide of the invention are also included herein, as long as the encoded polypeptide exhibits the activity or function of mcl-1 or the tissue expression pattern characteristic of mcl-1. Such polynucleotides include naturally occurring forms, such as allelic variants, and intentionally manipulated forms, for example, mutagenized polynucleotides, as well as artificially synthesized polynucleotides. Such mutagenized polynucleotides can be produced, for example, by subjecting mcl-1 polynucleotide to site-directed mutagenesis.

As described above, in another embodiment, a polynucleotide of the invention also includes in addition to mcl-1 coding regions, those nucleotides which flank the coding region of the mcl-1 structural gene. For example, a polynucleotide of the invention includes 5' regulatory nucleotide sequences and 3' untranslated sequences associated with the mcl-1 structural gene. Analogous to bcl-2 (Cotter, et al., *Blood*, 76:131, 1990), oligonucleotide primers such as those representing nucleotide sequences in the major breakpoint region (mbr) or the minor cluster region (mcr) which flank a translocation region are useful in the polymerase chain reaction (PCR) for amplifying and detecting translocations associated with the mcl-1 gene. The primers may represent untranslated nucleotide sequences which detect sequence junctions produced by translocation in various mcl-1 associated cell proliferative disorders, for example.

The polynucleotide sequence for mcl-1 also includes antisense sequences. The polynucleotides of the invention also include sequences that are degenerate as a result of the genetic code. There are 20 natural amino acids, most of which are specified by more than one codon. Therefore, as long as th amino acid sequence of mcl-1 results in a functional polypeptide (at least, in the case of the sense polynucleotide strand), all degenerate nucleotide sequences are included in the invention. Where the antisense polynucleotide is concerned, the invention embraces all antisense polynucleotides capable of inhibiting production of mcl-1 polypeptide.

The preferred mcl-1 cDNA clone of the invention is defined by a sequence of 3946 basepairs, in accord with the longest transcript of 3.8 kb. The preferred mcl-1 encoded protein is approximately 350 amino acids and has a molecular weight of approximately 37.5 kD. In its amino terminal portion, the mcl-1 protein contains two "PEST" sequences, enriched in proline (P), glutamic acid (E), serine (S), and threonine (T) and four pairs of arginines. "PEST" sequences are present in a variety of oncoproteins and other proteins that undergo rapid turn-over. These "PEST" sequences are not found in the bcl-2 encoding polynucleotide sequence and, thus, represent a characteristic feature of members of the mcl-1 polypeptide family. It is in the carboxyl region that mcl-1 has sequence homology to bcl-2 (35% amino acid identity and 59% similarity in 139 amino acid residues).

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucleic Acid Research*, 9:879, 1981).

A mcl-1 containing cDNA library can be screened by injecting the various cDNAs into oocytes, allowing sufficient time for expression of the cDNA gene products to occur, and testing for the presence of the desired cDNA expression product, for example, by using antibody specific for mcl-1 polypeptide or by using functional assays for mcl-1 activity and a tissue expression pattern characteristic of mcl-1. alternatively, a cDNA library can be screened indirectly for mcl-1 polypeptides having at least one epitope using antibodies specific for mcl-1. Such antibodies can be either polyclonally or monoclonally derived and used to detect expression product indicative of the presence of mcl-1 cDNA.

Screening procedures which rely on nucleic acid hybridization make is possible to isolate any gene sequence from any organism, provided the appropriate probe is available. Oligonucleotide probes, which correspond to a part of the sequence encoding the protein in question, can be synthesized chemically. This require that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding mcl-1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have bee denatured into a single-stranded form (Jay, et al., *Nucl. Acid Res.*, 11:2325, 1983).

A cDNA expression library, such as lambda gt11, can be screened indirectly for mcl-1 peptides having at lest one epitope, using antibodies specific for mcl-1. Such antibodies can be either polyclonally or monoclonally derived and used to detect expression product indicative of the presence of mcl-1 cDNA. DNA sequences encoding mcl-1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the mcl-1 polynucleotide sequences may be inserted into a recombinant expression vector. The term "recombinant expression vector" refers to a plasmid, virus or other vehicle known in the art that has been manipulated by insertion or incorporation of the mcl-1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding mcl-1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the mcl-1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes polyclonal and monoclonal antibodies immunoreactive with mcl-1 polypeptide or immunogenic fragments thereof. If desired, polyclonal antibodies can be further purified, for example, by binding to and elution from a matrix to which mcl-1 polypeptide is bound. Those of skill in the art will know of various other techniques common in the immunology arts for purification and/or concentration of polyclonal antibodies, as well as monoclonal antibodies. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975). The term antibody or, immunoglobulin as used in this invention includes intact molecules as well as fragments thereof, such as Fab and $F(ab')_2$, which are capable of binding an epitopic determinant on mcl-1.

A preferred method for the identification and isolation of antibody binding domain which exhibit binding with mcl-1 is the bacteriophage λ vector system. This factor system has been used to express a combinatorial library of Fab fragments from the mouse antibody repertoire in *Escherichia coli* (Huse, et al., *Science,* 246:1275–1281, 1989) and from the human antibody repertoire (Mullinax, et al., *Proc. Natl. Acad. Sci.,* 87:8095–8099, 1990). As described therein, receptors (Fab molecules) exhibiting binding for a preselected ligand were identified and isolated from these antibody expression libraries. This methodology can also be applied to hybridoma cell lines expressing monoclonal antibodies with binding for a preselected ligand. Hybridomas which secrete a desired monoclonal antibody can be produced in various ways using techniques well understood by those having ordinary skill in the art and will not be repeated here. Details of these techniques are described in such references as *Monoclonal Antibodies-Hybridomas: A New Dimension in Biological Analysis,* Edited by Roger H. Kennett, et al., Plenum Press, 1980; and U.S. Pat. No. 4,172,124.

The term "cell-proliferative disorder" denotes malignant as well as non-malignant cell populations which often appear to differ from the surrounding tissue both morphologically and genotypically. Such disorders may be associated, for example, with abnormal expression of mcl-1. "Abnormal expression" encompasses both increased or decreased levels of expression of mcl-1, as well as expression of a mutant form of mcl-1 such that the normal function of mcl-1 is altered. Abnormal expression also includes inappropriate expression of mcl-1 during the cell cycle or in an incorrect cell type. The mcl-1 polynucleotide in the form of an antisense polynucleotide is useful in treating malignancies of the various organ systems, particularly, for example, those of lymphoid origin such as lymphoma. Essentially, any disorder which is etiologically linked to altered expression of mcl-1 could be considered susceptible to treatment with a reagent of the invention which modulates mcl-1 expression. The term "modulate" envisions the suppression of expression of mcl-1 when it is over-expressed, or augmentation of mcl-1 expression when it is under-expressed or when the mcl-1 expressed is a mutant form of the polypeptide. When a cell proliferative disorder is associated with mcl-1 overexpression, such suppressive reagents as antisense mcl-1 polynucleotide sequence or mcl-1 binding antibody can be introduced to a cell. Alternatively, when a cell proliferative disorder is associated with underexpression or expression of a mutant mcl-1 polypeptide, a sense polynucleotide sequence (the DNA coding strand) or mcl-1 polypeptide can be introduced into the cell.

The invention provides a method for detecting a cell expressing mcl-1 or a cell proliferative disorder associated with mcl-1 comprising contacting a cell suspected of expressing mcl-1 or having a mcl-1 associated disorder, with a reagent which binds to the component. The cell component can be nucleic acid, such as DNA or RNA, or protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

For purposes of the invention, an antibody or nucleic acid probe specific for mcl-1 may be used to detect the presence of mcl-1 polypeptide (using antibody) or polynucleotide (using nucleic acid probe) in biological fluids or tissues. The use of oligonucleotide primers based on translocation regions in the mcl-1 sequence are useful for amplifying DNA, for example by PCR, and analysis of the translocation junctions. Any specimen containing a detectable amount of antigen can be used. A preferred sample of this invention is tissue of lymphoid origin, specifically tissue containing hematopoietic cells. More specifically, the hematopoietic cells are preferably myeloid cells. Preferably the subject is human.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

The method for detecting a cell expressing mcl-1 or a cell proliferative disorder associated with mcl-1, described above, can be utilized for detection of residual myeloid leukemia or other cells in a subject in a state of clinical remission. Additionally, the method for detecting mcl-1 polypeptide in cells is useful for detecting a cell proliferative disorder by identifying cells expressing mcl-1 at levels different than normal cells. Using the method of the invention, high, low, and mutant mcl-1 expression can be identified in a cell and the appropriate course of treatment can be employed (e.g., sense or antisense gene therapy).

The monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of mcl-1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

For purposes of the invention, mcl-1 may be detected by the monoclonal antibodies of the invention when present in biological fluids and tissues. Any sample containing a detectable amount of mcl-1 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

As used in this invention, the term "epitope" includes any determinant capable of specific interaction with the monoclonal antibodies of the invention. Epitopic determinants usually consist of chemically active surface groups of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the mcl-1 antigen for which the monoclonal antibodies are specific.

The concentration of detectably labeled monoclonal antibody which is administered should be sufficient such that the binding to those cells having mcl-1 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{137}$Gd, $^{55}$Mn, $^{162}$Dy, $^{52}$Cr, and $^{56}$Fe.

The monoclonal antibodies of the invention can be used to monitor the course of amelioration of mcl-1 associated cell proliferative disorder. Thus, by measuring the increase or decrease in the number of cells expressing mcl-1 or changes in the concentration of normal versus mutant mcl-1 present in various body fluids, it would be possible to determine whether a particular therapeutic regiment aimed at ameliorating the disorder is effective.

The present invention also provides a method for treating a subject with a mcl-1 associated cell proliferative disorder. The mcl-1 nucleotide sequence can be expressed in an altered manner as compared to expression in a normal cell, therefore it is possible to design appropriate therapeutic or diagnostic techniques directed to this sequence. Thus, where a cell-proliferative disorder is associated with the overexpression of mcl-1, nucleic acid sequences that interfere with mcl-1 expression at the translational level can be used. This approach utilizes, for example, antisense nucleic acid and ribozymes to block translation of a specific mcl-1 mRNA, either by masking that mRNA with an antisense nucleic acid or by cleaving it with a ribozyme. In cases when a cell proliferative disorder or abnormal cell phenotype is associated with the under expression of mcl-1 or expression of a mutant mcl-1 polypeptide, nucleic acid sequences encoding mcl-1 (sense) could be administered to the subject with the disorder.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to cause problems than larger molecules when introduced into the target mcl-1-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by mcl-1 protein. Such therapy would achieve its therapeutic effect by introduction of the mcl-1 antisense polynucleotide, into cells of subjects having the proliferative disorder. Delivery of antisense mcl-1 polynucleotide can be achieved using a recombinant expression vector such as a chimeric virus or a colloidal dispersion system. Disorders associated with under-expression of mcl-1 could similarly be treated using gene therapy with sense nucleotide sequences.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a mcl-1 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will known of, or can readily ascertain without undue experimentation, specific polynucleotide sequences which can be inserted into the retroviral genome to allow target specific delivery of the retroviral vector containing the mcl-1 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to $\Psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for mcl-1 antisense polynucleotides a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.,* 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectively, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies are preferred receptors. Antibodies can be used to target liposomes to specific cell-surface ligands. For example, certain antigens expressed specifically on tumor cells, referred to tumor-associated antigens (TAAs), may be exploited for the purpose of targeting mcl-1 antibody-containing liposomes directly to the malignant tumor. Since the mcl-1 gene product may be indiscriminate with respect to cell type in its action, a targeted delivery system offers a significant improvement over randomly injecting non-specific liposomes. Preferably, the target tissue is ovarian and the target cell is a granulosa cell. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to an the antigenic epitope on the target cells. Liposomes may also be targeted to cells expressing receptors for hormones or other serum factors.

The antibodies and substantially purified mcl-1 polypeptide of the present invention are ideally suited for the preparation of a kit. Such a kit may comprise a carrier means being compartmentalized to receive a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich immunoassays.

The term "immunometric assay" or "sandwich immunoassay", includes simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-mcl-1 immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blocker". The concentration of the "blockers" (normally 1–100 $\mu g/\mu l$) is important, in order to maintain the proper sensitivity yet inhibit any unwanted interference by mutually occurring cross reactive proteins in the specimen.

In addition to the polynucleotides of the invention, the monoclonal antibodies of the invention can also be used, alone or in combination with effector cells (Douillard, et al., *Hybridoma*, 5 Supp.1:S139, 1986), for immunotherapy in an animal having a cell proliferative disorder which expresses mcl-1 polypeptide with epitopes reactive with the monoclonal antibodies of the invention.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986) and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, and vinblastine.

The proteinaceous drugs with which the monoclonal antibodies of the invention can be labeled include immunomodulators and other biological response modifiers. The term "biological response modifiers" encompasses substances which are involved in modifying the immune response in such manner as to enhance the destruction of an mcl-1-associated tumor for which the monoclonal antibodies of the invention are specific. Examples of immune response modifiers include such compounds as lymphokines. Lymphokines include tumor necrosis factor, the interleukins, lymphotoxin, macrophage activating factor, migration inhibition factor, colony stimulating factor, and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy certain isotypes may be more preferable than others depending on such factors as tumor cell distribution as well as isotope stability and emission. If desired, the tumor cell distribution can be evaluated by the in vivo diagnostic techniques described above. Depending on the cell proliferative disease some emitters may be preferable to others. In general, alpha and beta particles emitting radioisotopes are preferred in immunotherapy. For example, if an animal has solid tumor foci a high energy beta emitter capable of penetrating several millimeters of tissue, such as $^{90}Y$, may be preferable. On the other hand, if the cell proliferative disorder consists of simple target cells, as in the case of leukemia, a short range, high energy alpha emitter, such as $^{212}Bi$, may be preferable. Examples of radioisotopes which can be bound to the monoclonal antibodies of the invention for therapeutic purposes are $^{125}I$, $^{131}I$, $^{90}Y$, $^{67}Cu$, $^{212}Bi$, $^{211}At$, $^{212}Pb$, $^{47}Sc$, $^{109}Pd$, and $^{188}Re$.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms, that, in sufficient dose, are often lethal. Diphtheria toxin is a substance produced by *Corynebacterium diphtheria* which can be used therapeutically. The toxin consists of an alpha and beta subunit which under proper conditions can be separated. The toxic A component can be bound to an antibody and used for site specific delivery to a mcl-1 bearing cell for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner, et al., *Science*, 235:895, 1987). Alternatively, the monoclonal antibody of the invention could be used, for example, in combination with gamma-interferon to thereby activate and increase the expression of Fc receptors by effector cells which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibody of the invention.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and half-life of the agent.

Using monoclonal antibodies of the invention, it is possible to design therapies combining all of the characteristics described herein. For example, in a given situation it may be desirable to administer a therapeutic agent, or agents, prior to the administration of the monoclonal antibodies of the invention in combination with effector cells and the same, or different, therapeutic agent or agents. For example, it may be desirable to treat patients with leukemia or lymphoma by first administering gamma-interferon and interleukin-2 daily for 3 to 5 days, and on day 5 administer the monoclonal antibody of the invention in combination with effector cells as well as gamma-interferon, and interleukin-2.

It is also possible to utilize liposomes with the monoclonal antibodies of the invention in their membrane to specifically deliver the liposome to the area of the tumor expressing mcl-1. These liposomes can be produced such that they contain, in addition to the monoclonal antibody, such immunotherapeutic agents as those described above which would then be released at the tumor site (Wolff, et al., *Biochemical et Biophysical Acta*, 802:259, 1984).

The dosage ranges for the administration of monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the polynucleotides or the monoclonal antibodies of the invention, the medicament being used for therapy of mcl-1 associated cell proliferative disorders.

The invention also provides a method of preventing programmed cell death (apoptosis) in a cell comprising introducing into the cell, functional mcl-1 polypeptide or an expression vector containing an mcl-1 encoding polynucleotide sequence. For example, this method can be used to increase the viability of the cell in cell culture during an ex vivo protocol or for long term in vitro cell propagation. Similarly, introduction of mcl-1 polypeptide or an expression vector containing the mcl-1 encoding polynucleotide sequence into a cell can be utilized as a means for inducing differentiation in a cell capable of undergoing differentiation.

The following example are intended to illustrate but not limit the invention. While they are typical of those that might be used, other procedures known to those skilled in the art may alternatively be used.

EXAMPLE 1

Construction and Screening of TPA Induced ML-1 Cell cDNA Library

To identify "early-induction" genes, poly(A)+ RNA was isolated from ML-1 cells induced with TPA for three hours. A complementary DNA (cDNA) library was constructed and was screened by differential hybridization, using probes derived from the TPA-induced cells AND uninduced controls. A cDNA clone representing mcl-1 was identified based upon preferential hybridization to the probe from induced cells.

ML-1 cells were programmed to differentiate with TPA as described previously (K. M. Kozopas, H. L. Buchan, R. W. Craig, *J. Cell Physiol.*, 145, 575 (1990). After preincubation under reduced serum conditions for 3 days, cells were exposed to $5 \times 10^{-10}$ M TPA for 3 hours. Poly(A)+ RNA from these TPA-induced cells was used for oligo(dT)-primed first strand cDNA synthesis, which was carried out with Moloney murine leukemia virus reverse transcriptase (Bethesda Research Laboratories, Gaithersburg, Md.). After second strand cDNA synthesis, double stranded cDNA of >500 basepairs was cloned into the EcoRI site of lambda gt10. The library obtained was subjected to differential screening, using $^{32}$P-labeled cDNA probes synthesized by reverse transcription of poly(A)$^+$ RNA from the TPA-induced cells and a parallel culture of uninduced cells. A clone exhibiting preferential hybridization to the probe from induced cells (clone dif8C, containing nucleotides 3150–3946 of mcl-1) was isolated and subcloned into the Bluescript plasmid (Stratagene, La Jolla, Calif.). This clone was used to rescreen the cDNA library to obtain clones spanning the mcl-1 cDNA. Clones spanning the mcl-1 coding region were also obtained from a cDNA library from TPA-induced U-937 cells (Clontech, Palo Alto, Calif.). Sequencing was carried out using the Sequenase enzyme (U.S. Biochemicals, Cleveland, Ohio).

EXAMPLE 2

Time Course of Expression of mcl-1

The time course of expression of mcl-1 was monitored during the differentiation of ML-1 cells. ML-1 cells were exposed to 5×10$^{-10}$ M TPA and assayed at various times for expression of mcl-1 and other mRNAs (Panels A, B) and for cell surface markers of differentiation (Panel C). Panel A shows expression of mcl-1 as determined by Northern blotting. Probes for mcl-1 (dif8C-p3.2, see FIG. 3), beta-actin, myb (pCM8), and CD11b were hybridized to total RNA from cells exposed to TPA for the indicated times [in hours (h) or days (d)]. Panel B shows the time course of expression of mcl-1. Autoradiographs such as the one shown in (A) were subjected to densitometric scanning. The values for expression of mcl-1 were normalized by dividing by the corresponding value for beta-actin, which did not change with time. Relative expression of mcl-1 was estimated as the ratio of expression in TPA-induced cells to that in uninduced controls. Panel C shows the time course of appearance of cell surface markers of differentiation. Flow cytometry (FACSCAN) was performed using phycoerythrin-conjugated antibodies to CD11b and CD14 (Becton Dickenson, Mountain View, Calif.). Background fluorescence, determined using isotype matched control antibodies, was subtracted. The percentage of morphologically differentiating cells averaged 40%, 82%, and 90% in cultured induced with TPA for 1, 2, and 3 days, respectively, and 3.5% in uninduced control cultures, as found previously. These differentiating cells were predominantly immature forms on day 1, with approximately equal numbers of immature and mature forms present on days 2 and 3. Cell growth in the TPA-induced culture was decreased by about 93%, as found previously. Each point represents the average ±SE of 2–5 experiments.

Figure 1C:
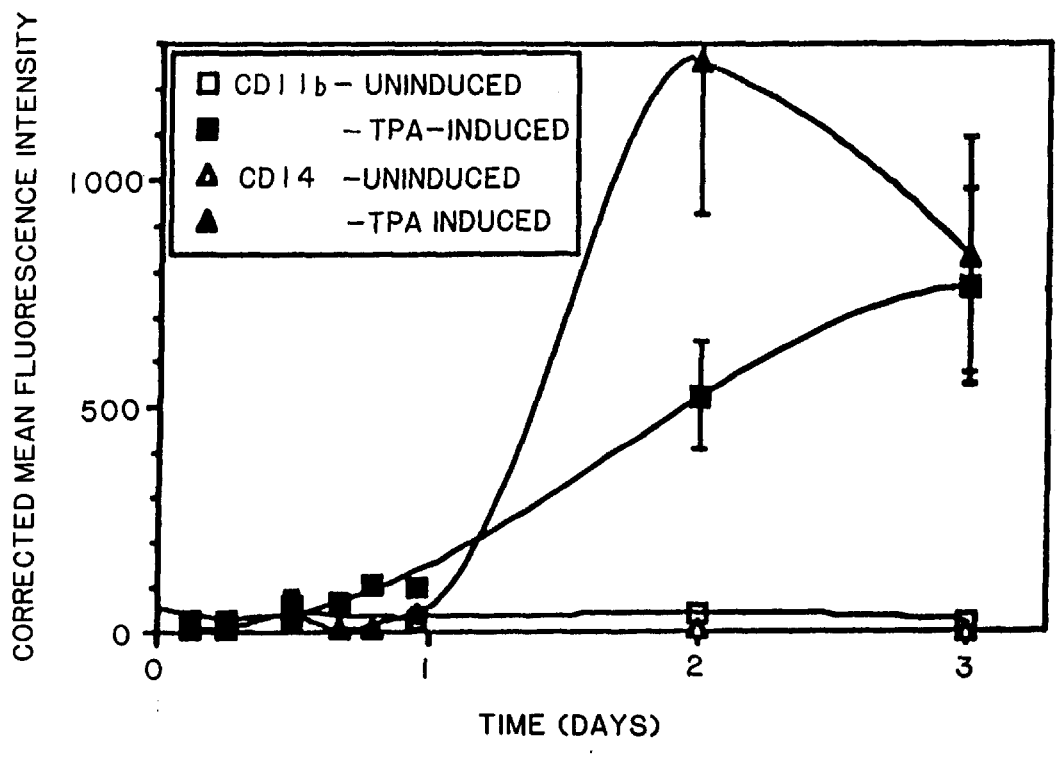

While expression of mcl-1 was low in uninduced cells, it increased dramatically early in induction with TPA (FIG. 1A). This increase was seen within one hour and was maximal (>6-fold at 3 hours) (FIG. 1B). At this time, the programming of differentiation was in progress and expression of c-myb mRNA was decreased (Craig, et al., Ca. Res., 44:442, 1984), although no changes in morphology or differentiation markers had occurred (FIGS. 1A, C). These markers did not begin to appear until 16–24 hours (FIG. 1C), when expression of mcl-1 was in decline [to <50% of maximum (FIGS. 1A, B)]. Expression of mcl-1 also increased early in the TPA-induced differentiation of other myeloid leukemia cell lines, including HL-60, and U-937. The rapid up-regulation and down-regulation of this "early-induction" gene prior to phenotypic differentiation is thus reminiscent of the pattern of expression of the "early-response" genes important in proliferation (Nathans, et al., Cold Spring Harbor Symposia on Quantitative Biology LIII, pp. 893–900, 1988).

The genes in the mcl-1/bcl-2 family exhibit intriguing parallels in their patterns of expression. mcl-1 was isolated from ML-1 cells, which are derived from a patient who developed acute myeloid leukemia after the remission of a T-cell lymphoma; bcl-2 was originally identified in patients with follicular B-cell lymphoma. TPA elicited an early increase in expression of mcl-1 (FIG. 1), and can combine with other agents to cause similar increases in bcl-3 and BHRF1. Expression of mcl-1 is increased early in myeloid cells programmed to differentiate and stop proliferating without dying (FIG. 1). Expression of bcl-2 is increased in lymphoid cells programmed to remain viable and selected for further differentiation. Expression of BHRF1 is increased early in the lytic cycle of the virus and early in serum-induced stimulation of proliferation. Genes i the mcl-1/bcl-2 family are thus characterized, not only by homology in the carboxyl region/hydrophobic tail (FIG. 4), but also by the fact that changes in expression may occur as an early event in the programs that determine call proliferation, differentiation, and/or viability.

It is not yet known how these parallels in patterns of expression might translate into parallels in function. bcl-2 has a role in the maintenance of viability through inhibition of programmed cell death; it appears to operate in a variety of cells, including hematopoietic cell lines deprived of required growth factors, certain types of B-cells (e.g., B-memory cells), and T-cells under specific circumstances. The identification of mcl-1 allows it to be tested for a similar role in the maintenance of viability, apparently operating in myeloid cells during the induction of differentiation. bcl-2 is distinct from many oncogenes and growth-factor related genes in that it can enhance viability without stimulation proliferation; the viable cells remain in $G_0/G_1$ phase of the cell cycle. mcl-1 may also play a role in the accumulation in $G_0/G_1$ that accompanies differentiation. Deregulation of bcl-2 is thought to contribute to tumorigenesis by increasing cell survival, thereby increasing the probability of accumulation of additional changes (such as rearrangements of the c-myc oncogene). The discovery of the related mcl-1 gene leads to the identification of a growing number of genes which affect the programming of cell death and/or differentiation. These genes may prove to be as important, in tumorigenesis and its reversal, as the wide variety of known families of oncogene and tumor suppressor genes.

EXAMPLE 3

Sequence of mcl-1

Figure 5A:
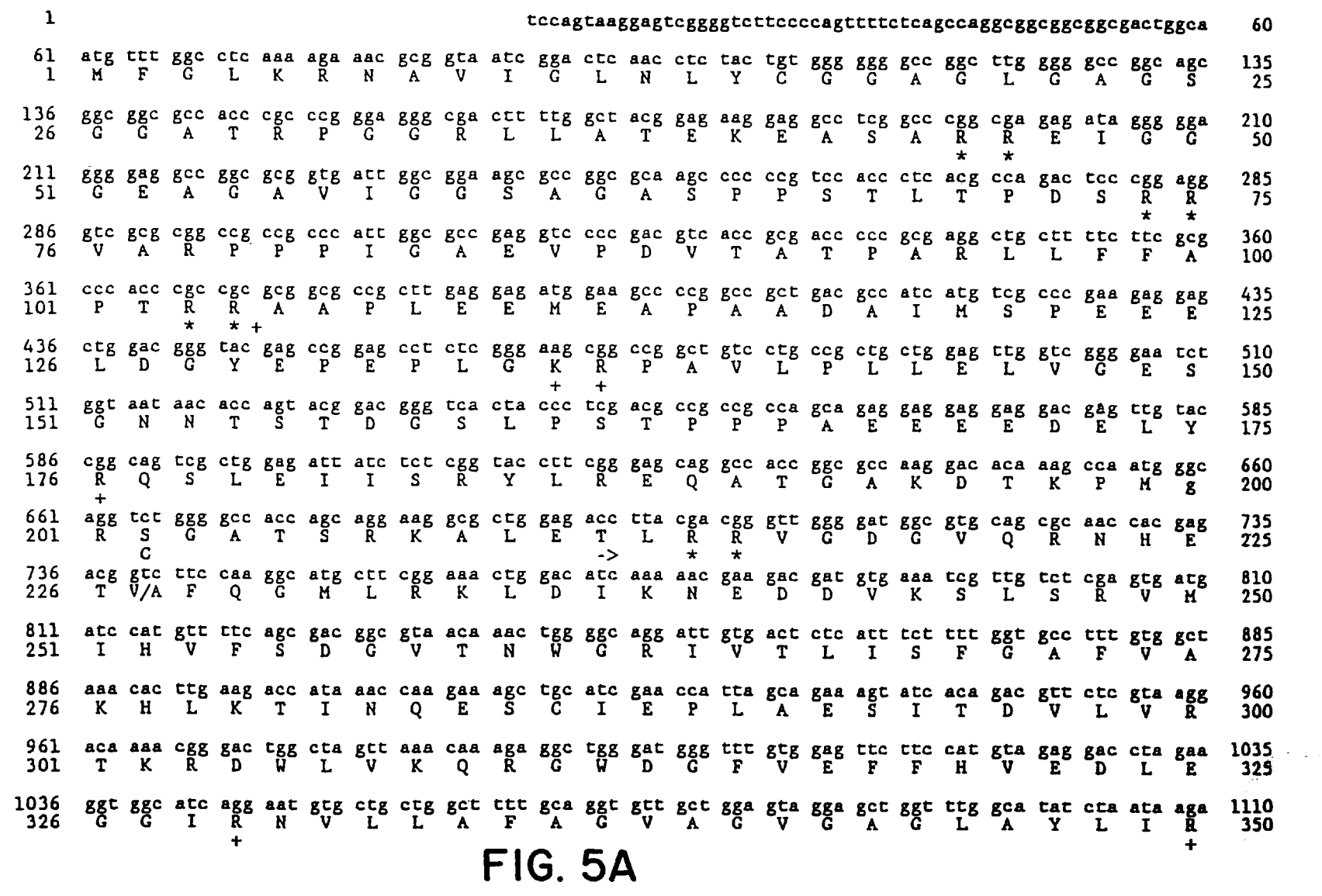
Figure 5B:
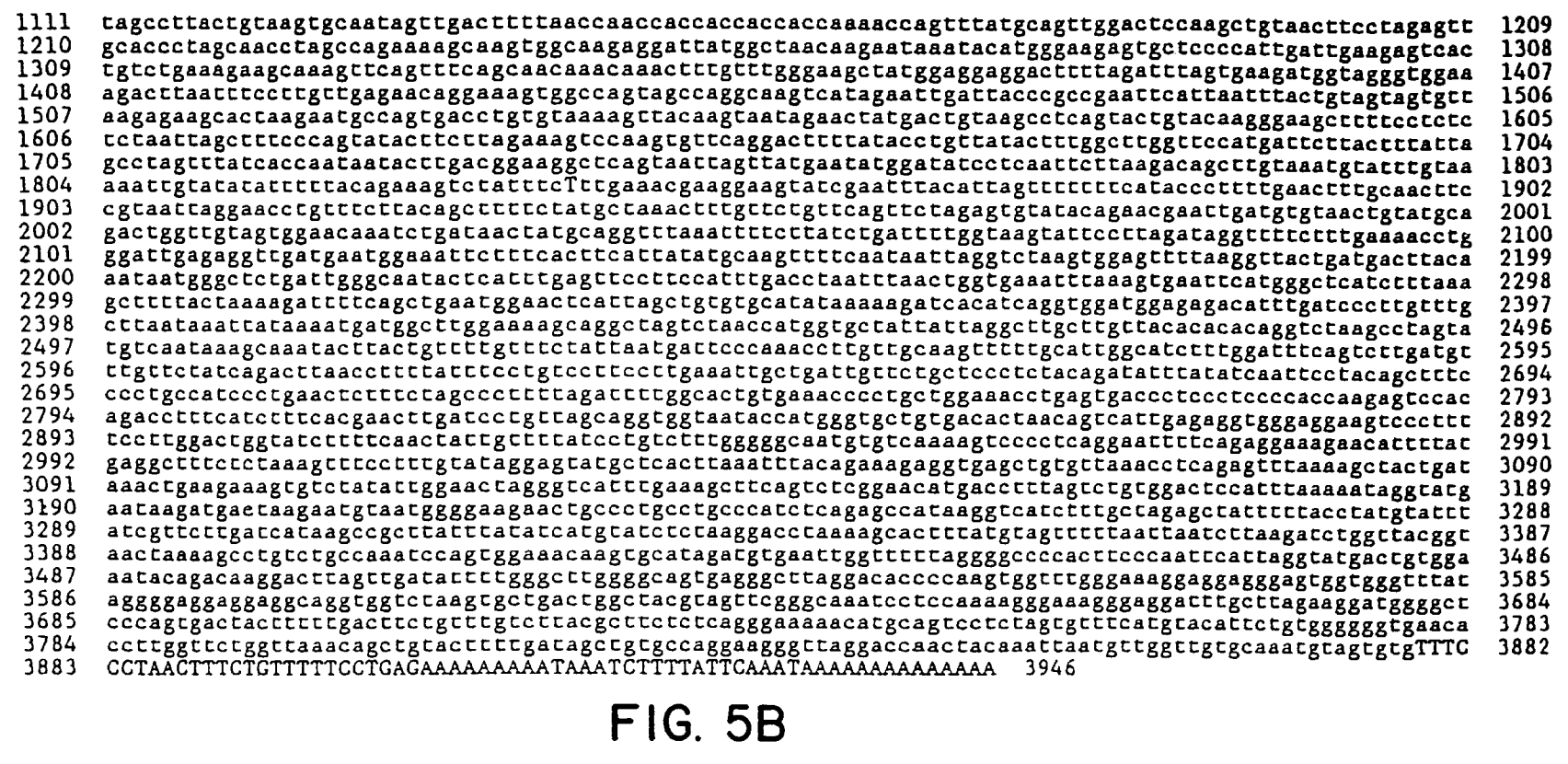

A panel of overlapping mcl-1 cDNA clones was initially obtained. These clones defined a sequence of 3,946 basepairs, in accord with the longest transcript size of 3.8 kb (FIGS. 5a and 5b). The longest open reading frame within this sequence is preceded by a Kozak sequence (Kozak, Nucl. Acids Res., 12:857, 1984) and an upstream in-frame stop codon. Several polymorphisms exist in the nucleotide sequence. When nucleotide 740 is C, amino acid 227 is alanine (A); when nucleotide 740 is T, amino acid 227 is valine (V). Using this reading frame, the mcl-1-encoded protein (FIG. 2A) was predicted to contain 350 amino acids and to have a molecular size of 37.3 kD. FIG. 2 shows the deduced amino acid sequence of the mcl-1 protein and schematic representation of the cDNA. In panel A, PEST sequences are underlined and asterisks indicate pairs of arginines. The arrow indicates the region with homology to bcl-2 and double lines indicate the hydrophobic carboxyl tail. Plus signs indicate positively charge flanking amino acid resides. Amino acid residue 227 was valine in clones from ML-1 and alanine in those from U-937. Amino acid residue 1 corresponds to nucleotides 61–63 of the cDNA. Panel B shows a schematic representation of mcl-1. The boxed area represents the protein coding region; this is followed by a line representing the 3'-untranslated region (discontinuous line). The amino terminus of mcl-1 has some characteristics of a signal sequence (as does that of BHRF1) , but does not function as such in in vitro translation in the presence of microsomal membranes.

Figure 2B:
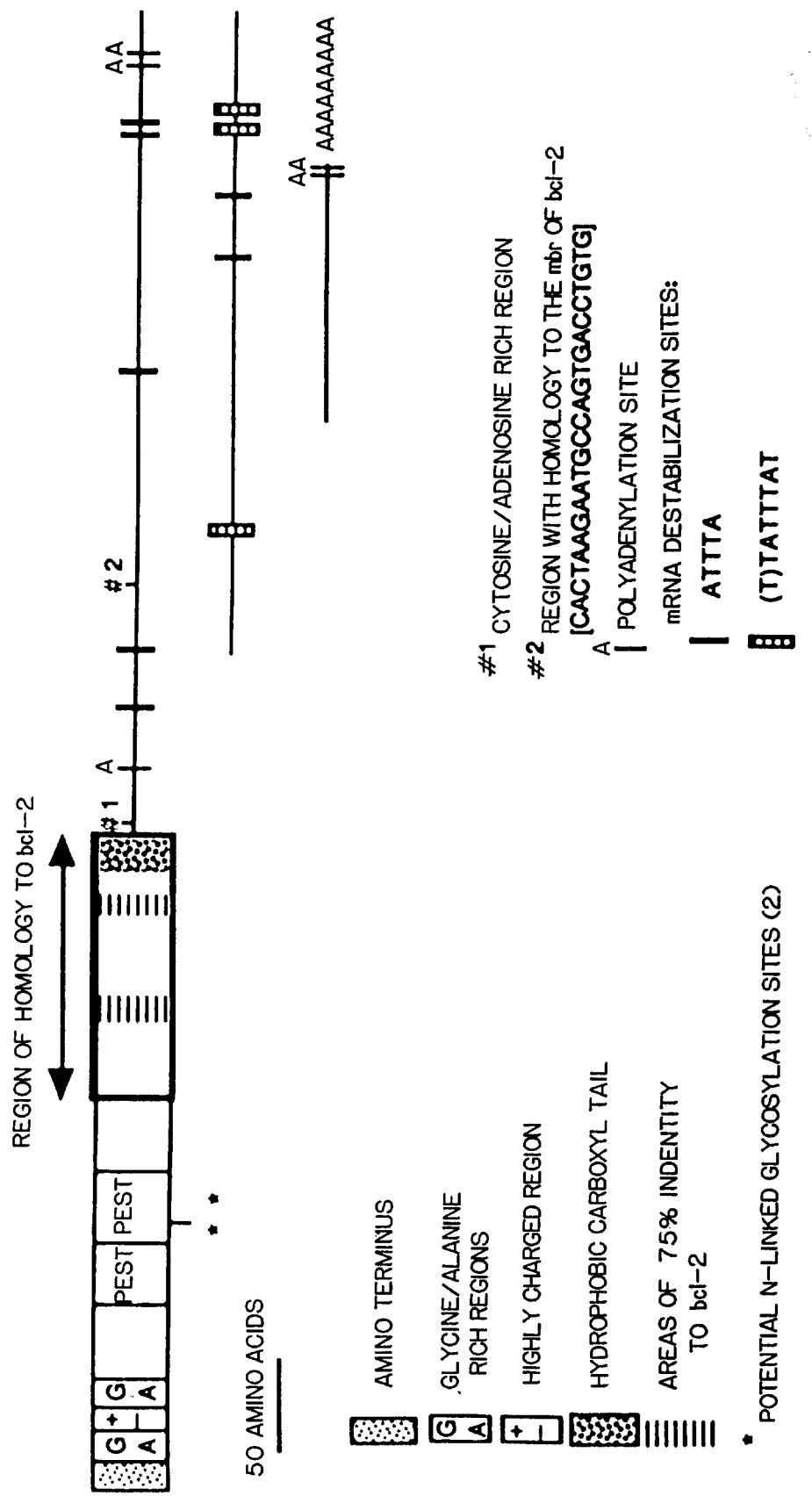

Parallels within this family continue downstream of the protein coding region: Both mcl-1 and bcl-2 have long 3'-untranslated regions [2.8 kb in mcl-1 (FIG. 2B)]. Both have multiple potential polyadenylation sites and mRNA destabilization signals. The presence of several polyadenylation sites in mcl-1 (FIG. 2B) might relate to the two transcripts observed (FIG. 1A). The presence of mRNA destabilization signals might relate to the transience of the increase in expression (FIGS. 1A, B). Translocations involving bcl-2 frequently occur in the 340 -untranslated region, often within the "major breakpoint region" (mbr) of about 150 nucleotides. Interestingly, the 3'-untranslated region of mcl-1 contains a stretch with sequence similarity to this mbr (FIG. 2B).

Figure 3:
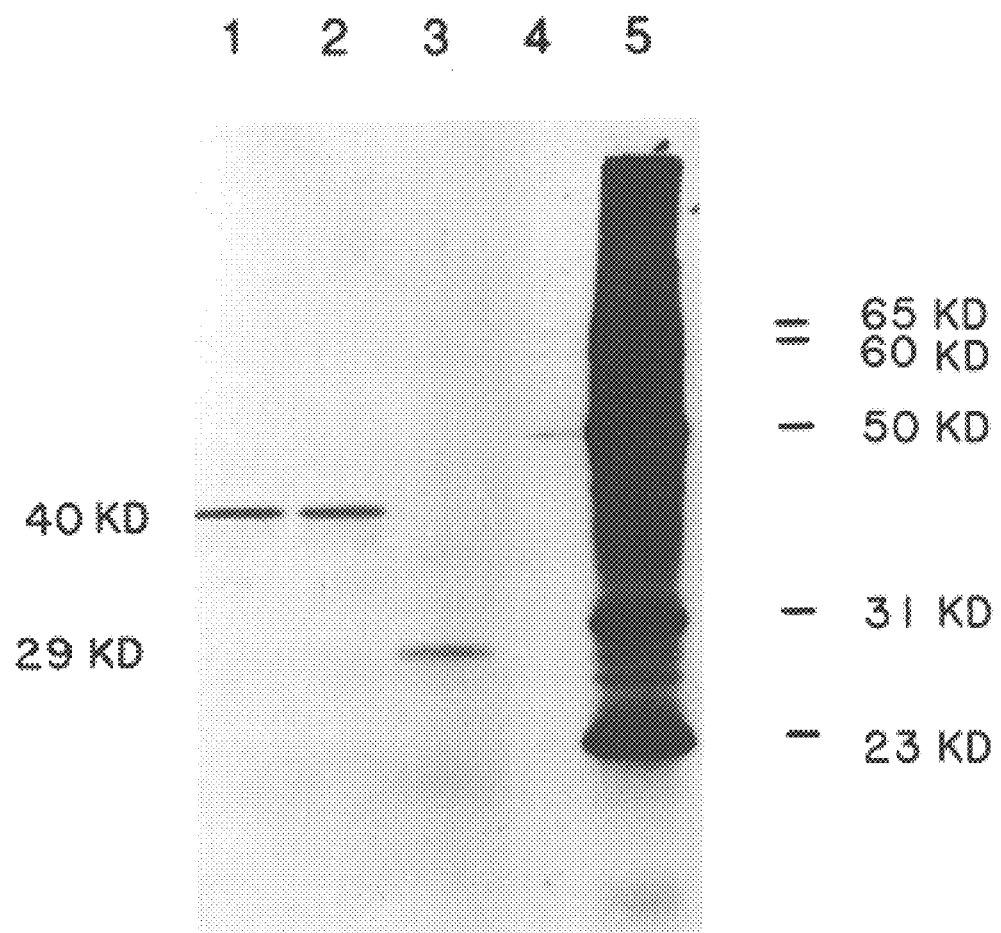
FIG. 3 shows in vitro translation of mcl-1 mRNA.

The size of mcl-1 encoded protein was confirmed by in vitro translation using mcl-1 cDNAs from two independent sources (FIG. 3, lanes 1–2). FIG. 3 in vitro translation of mcl-1 mRNA. A cDNA lacking the first methionine yielded a truncated protein of the size predicted from the second methionine (FIG. 3, lane 3). Plasmids representing mcl-1 were linearized at the 3' end of the cDNA and used to prepare mRNA by in vitro transcription with T7 polymerase (Pharmacia, Piscataway, N.J.). This mRNA was translated in vitro in the presence of $^{35}$S-methionine (1000 Ci/mmol, Amersham, Arlington Heights, Ill.), using a rabbit reticulocyte lysate system (Novagen, Madison, Wis.). The reaction products were separately by sodium dodecyl sulfate polyacrylamide (12.5%) gel electrophoresis and detected by autoradiography. Lane 1 shows reaction products from a cDNA containing the complete mcl-1 coding sequence (clone dif8C-1A6, containing nucleotides 52 to 1484). Lane 2 shows reaction product s from a different cDNA clone (clone dif8C-3.2, containing nucleotides 7 to 1484). Lane 3 shows reaction products from a cDNA clone lacking the methionine at amino acid residue 1 (clone dif8C-7C, containing nucleotides 278 to 1484). Clones dif8C-1A6 and dif8C-7C were from the cDNA library from U-937 cells; clone dif8C-3.2 was from the cDNA library from ML-1 cells. Lane 4 shows no mRNA and lane 5 shows the molecular weight markers. (Traces of the marker are also present in lane 4).

In its amino terminal portion, the predicted mcl-1 protein contains several interesting features, including two "PEST" sequences (Rogers, et al., *Science*, 234:364, 1986), enriched in proline (P), glutamic acid (E), serine (S), and threonine (T) and four pairs of arginines (FIGS. 2, 2A, B). These sequences are present in a variety of oncoproteins and other proteins that undergo rapid turn-over. Their presence in mcl-1 suggests that this protein might be expected to be expressed, like the mRNA (FIG. 1), primarily in the early stages of differentiation. Interestingly, bcl-2 does not have PEST sequences, although it does demonstrate differentiation-stage specific expression (e.g., in myeloid cells and intestinal epithelium, where expression declines during maturation).

It is in the carboxyl region that mcl-1 has sequence homology to bcl-2 [35% amino acid identity and 59% similarity in 139 amino acid residues, FIG. 2A, B (arrows) and FIG. 4]. FIG. 4 shows the alignment of the carboxyl portions of mcl-1, bcl-2, and BHRF1. The BESTFIT program (GCG Sequence Analysis Software) was used to align the amino acid sequences of the carboxyl portions of mcl-1, bcl-2alpha [human (Tsujimoto, et al., *Proc. Natl. Acad. Sci. USA*, 83:5214, 1986)] and BHRF 1 [Epstein-Barr virus (Pearson et al., *Virology*, 160:151, 1987)], gaps being inserted to maximize overlap. The symbols used are: |=amino acid identity; :=amino acid comparison value $\geq 0.5$; .=amino acid comparison value $\geq 0.1$. Bold letters indicate residues that are identical in the three proteins. Double lines flanked by plus signs indicate the hydrophobic carboxyl tail. Asterisks indicate areas of high conservation; a consensus sequence for mcl-1 and bcl-2 is shown at the top, where conserved non-identical residues are indicated as follows: a=P, A, G, S, T; i=L, I, V, M; f=F, Y, W; d=Q, N, E, D; h=H, K, R, as determined by the SIMPLIFY program. Differences in reported sequences of bcl-2 are in underlined italics. Differences between human and mouse (Negrini, et al., *Cell*, 49:455, 1987) bcl-2 are double underlined.

bcl-2 was identified in follicular B-cell lymphomas, the majority of which have a specific translocation involving chromosomes 14 and 18. This translocation juxtaposes bcl-2 with the immunoglobulin heavy chain locus and results in deregulated expression of an unaltered bcl-2 gene product. bcl-2 has not been found to have homology to previously described cellular oncogenes or to contain motifs characteristic of other known gene families. The carboxyl region of bcl-2 is known to exhibit some homology to the BHRF1 gene from Epstein-Barr virus (25%), and this parallels the fact that the carboxyl regions of human and mouse bcl-2 exhibit greater identity (98% in 144 amino acid residues) than do the amino terminal portions (76%). Thus, the discovery of mcl-1 provides the first example of a cellular gene with homology to bcl-2 and suggests the existence of a unique gene family represented by mcl-1, bcl-2, and BHRF-1. Homology in the carboxyl region appears to be an important defining characteristic of this family.

At their extreme carboxyl termini, mcl-1, bcl-2 (bcl-2alpha), and BHRF1 each contain a potential membrane spanning domain (20 hydrophobic amino acid residues indicated with double lines and flanked by positively charged residues in FIGS. 2A and 4). This hydrophobic carboxyl tail is known to mediate the membrane-association of bcl-2, which has recently been localized to mitochondrial membranes (Hockenberg, et al., *Nature*, 348:334, 1990). BHRF-1 is also membrane-associated. The finding of a hydrophobic carboxyl tail in mcl-1 suggests that the potential for membrane association may be another important characteristic of genes in this family.

The foregoing is meant to illustrate, but not to limit, the scope of the invention. Indeed, those of ordinary skill in the art can readily envision and produce further embodiments, based on the teachings herein, without undue experimentation.

What is claimed is:

1. A method for identifying a cell expressing mcl-1 polypeptide comprising contacting the cell with a reagent which binds to the polypeptide, and detecting binding of the reagent, thereby identifying a cell expressing mcl-1.

2. The method of claim 1, wherein the reagent is a probe.

3. The method of claim 2, wherein the probe is an antibody.

4. The method of claim 3, wherein the antibody is polyclonal.

5. The method of claim 3, wherein the antibody is monoclonal.

6. The method of claim 1, wherein the cell is a hematopoietic cell.

7. The method of claim 2, wherein the probe is detectably labeled.

8. The method of claim 7, wherein the label is selected from the group consisting of a radioisotope, a bioluminescent compound, a chemiluminescent compound, a fluorescent compound, a metal chelate, or an enzyme.

\* \* \* \* \*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 3946 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: mcl-1

(ix) FEATURE:
        (A) NAME/KEY: CDS
        (B) LOCATION: 61..1110
        (D) OTHER INFORMATION: /note= "When nucleotide 740 = C,
           amino acid 227 = A; when nucleotide 740 = T, amino
           acid 227 = V."

(xi) SEQUENCE DESCRIPTION: SEQ ID NO:1:

```
TCCAGTAAGG AGTCGGGGTC TTCCCCAGTT TTCTCAGCCA GGCGGCGGCG GCGACTGGCA      60
ATGTTTGGCC TCAAAAGAAA CGCGGTAATC GGACTCAACC TCTACTGTGG GGGGCCGGC      120
TTGGGGCCG GCAGCGGCGG CGCCACCCGC CCGGGAGGGC GACTTTTGGC TACGGAGAAG      180
GAGGCCTCGG CCCGGCGAGA GATAGGGGGA GGGGAGGCCG GCGCGGTGAT TGGCGGAAGC      240
GCCGGCGCAA GCCCCCCGTC CACCCTCACG CCAGACTCCC GGAGGGTCGC GCGGCCGCCG      300
CCCATTGGCG CCGAGGTCCC CGACGTCACC GCGACCCCCG CGAGGCTGCT TTTCTTCGCG      360
CCCACCCGCC GCGCGGCGCC GCTTGAGGAG ATGGAAGCCC CGGCCGCTGA CGCCATCATG      420
TCGCCCGAAG AGGAGCTGGA CGGGTACGAG CCGGAGCCTC TCGGGAAGCG GCCGGCTGTC      480
CTGCCGCTGC TGGAGTTGGT CGGGGAATCT GGTAATAACA CCAGTACGGA CGGGTCACTA      540
CCCTCGACGC CGCCGCCAGC AGAGGAGGAG GAGGACGAGT TGTACCGGCA GTCGCTGGAG      600
ATTATCTCTC GGTACCTTCG GGAGCAGGCC ACCGGCGCCA AGGACACAAA GCCAATGGGC      660
AGGTCTGGGG CCACCAGCAG GAAGGCGCTG GAGACCTTAC GACGGGTTGG GGATGGCGTG      720
CAGCGCAACC ACGAGACGGT CTTCCAAGGC ATGCTTCGGA AACTGGACAT CAAAAACGAA      780
GACGATGTGA AATCGTTGTC TCGAGTGATG ATCCATGTTT TCAGCGACGG CGTAACAAAC      840
TGGGGCAGGA TTGTGACTCT CATTTCTTTT GGTGCCTTTG TGGCTAAACA CTTGAAGACC      900
ATAAACCAAG AAAGCTGCAT CGAACCATTA GCAGAAAGTA TCACAGACGT TCTCGTAAGG      960
ACAAAACGGG ACTGGCTAGT TAAACAAAGA GGCTGGGATG GGTTTGTGGA GTTCTTCCAT     1020
GTAGAGGACC TAGAAGGTGG CATCAGGAAT GTGCTGCTGG CTTTTGCAGG TGTTGCTGGA     1080
GTAGGAGCTG GTTTGGCATA TCTAATAAGA TAGCCTTACT GTAAGTGCAA TAGTTGACTT     1140
TTAACCAACC ACCACCACCA CCAAAACCAG TTTATGCAGT TGGACTCCAA GCTGTAACTT     1200
CCTAGAGTTG CACCCTAGCA ACCTAGCCAG AAAAGCAAGT GGCAAGAGGA TTATGGCTAA     1260
CAAGAATAAA TACATGGGAA GAGTGCTCCC CATTGATTGA AGAGTCACTG TCTGAAAGAA     1320
GCAAAGTTCA GTTTCAGCAA CAAACAAACT TTGTTTGGGA AGCTATGGAG GAGGACTTTT     1380
AGATTTAGTG AAGATGGTAG GGTGGAAAGA CTTAATTTCC TTGTTGAGAA CAGGAAAGTG     1440
GCCAGTAGCC AGGCAAGTCA TAGAATTGAT TACCCGCCGA ATTCATTAAT TTACTGTAGT     1500
```

-continued

```
AGTGTTAAGA GAAGCACTAA GAATGCCAGT GACCTGTGTA AAAGTTACAA GTAATAGAAC    1560

TATGACTGTA AGCCTCAGTA CTGTACAAGG GAAGCTTTTC CTCTCTCTAA TTAGCTTTCC    1620

CAGTATACTT CTTAGAAAGT CCAAGTGTTC AGGACTTTTA TACCTGTTAT ACTTTGGCTT    1680

GGTTCCATGA TTCTTACTTT ATTAGCCTAG TTTATCACCA ATAATACTTG ACGGAAGGCT    1740

CAGTAATTAG TTATGAATAT GGATATCCTC AATTCTTAAG ACAGCTTGTA AATGTATTTG    1800

TAAAAATTGT ATATATTTTT ACAGAAAGTC TATTTCTTTG AAACGAAGGA AGTATCGAAT    1860

TTACATTAGT TTTTTTCATA CCCTTTTGAA CTTTGCAACT TCCGTAATTA GGAACCTGTT    1920

TCTTACAGCT TTTCTATGCT AAACTTTGTT CTGTTCAGTT CTAGAGTGTA TACAGAACGA    1980

ATTGATGTGT AACTGTATGC AGACTGGTTG TAGTGGAACA AATCTGATAA CTATGCAGGT    2040

TTAAATTTTC TTATCTGATT TTGGTAAGTA TTCCTTAGAT AGGTTTTCTT TGAAAACCTG    2100

GGATTGAGAG GTTGATGAAT GGAAATTCTT TCACTTCATT ATATGCAAGT TTTCAATAAT    2160

TAGGTCTAAG TGGAGTTTTA AGGTTACTGA TGACTTACAA ATAATGGGCT CTGATTGGGC    2220

AATACTCATT TGAGTTCCTT CCATTTGACC TAATTTAACT GGTGAAATTT AAAGTGAATT    2280

CATGGGCTCA TCTTTAAAGC TTTTACTAAA AGATTTTCAG CTGAATGGAA CTCATTAGCT    2340

GTGTGCATAT AAAAAGATCA CATCAGGTGG ATGGAGAGAC ATTTGATCCC TTGTTTGCTT    2400

AATAAATTAT AAAATGATGG CTTGGAAAAG CAGGCTAGTC TAACCATGGT GCTATTATTA    2460

GGCTTGCTTG TTACACACAC AGGTCTAAGC CTAGTATGTC AATAAAGCAA ATACTTACTG    2520

TTTTGTTTCT ATTAATGATT CCCAAACCTT GTTGCAAGTT TTTGCATTGG CATCTTTGGA    2580

TTTCAGTCTT GATGTTTGTT CTATCAGACT TAACCTTTTA TTTCCTGTCC TTCCTTGAAA    2640

TTGCTGATTG TTCTGCTCCC TCTACAGATA TTTATATCAA TTCCTACAGC TTTCCCCTGC    2700

CATCCCTGAA CTCTTTCTAG CCCTTTTAGA TTTTGGCACT GTGAAACCCC TGCTGGAAAC    2760

CTGAGTGACC CTCCCTCCCC ACCAAGAGTC CACAGACCTT TCATCTTTCA CGAACTTGAT    2820

CCTGTTAGCA GGTGGTAATA CCATGGGTGC TGTGACACTA ACAGTCATTG AGAGGTGGGA    2880

GGAAGTCCCT TTTCCTTGGA CTGGTATCTT TTCAACTATT GTTTTATCCT GTCTTTGGGG    2940

GCAATGTGTC AAAAGTCCCC TCAGGAATTT TCAGAGGAAA GAACATTTTA TGAGGCTTTC    3000

TCTAAAGTTT CCTTTGTATA GGAGTATGCT CACTTAAATT TACAGAAAGA GGTGAGCTGT    3060

GTTAAACCTC AGAGTTTAAA AGCTACTGAT AAACTGAAGA AAGTGTCTAT ATTGGAACTA    3120

GGGTCATTTG AAAGCTTCAG TCTCGGAACA TGACCTTTAG TCTGTGGACT CCATTTAAAA    3180

ATAGGTATGA ATAAGATGAC TAAGAATGTA ATGGGGAAGA ACTGCCCTGC CTGCCCATCT    3240

CAGAGCCATA AGGTCATCTT TGCTAGAGCT ATTTTTACCT ATGTATTTAT CGTTCTTGAT    3300

CATAAGCCGC TTATTTATAT CATGTATCTC TAAGGACCTA AAAGCACTTT ATGTAGTTTT    3360

TAATTAATCT TAAGATCTGG TTACGGTAAC TAAAAGCCTG TCTGCCAAAT CCAGTGGAAA    3420

CAAGTGCATA GATGTGAATT GGTTTTTAGG GGCCCCACTT CCCAATTCAT TAGGTATGAC    3480

TGTGGAAATA CAGACAAGGA CTTAGTTGAT ATTTGGGCT TGGGGCAGTG AGGGCTTAGG    3540

ACACCCCAAG TGGTTTGGGA AAGGAGGAGG GAGTGGTGGG TTTATAGGGG AGGAGGAGGC    3600

AGGTGGTCTA AGTGCTGACT GGCTACGTAG TTCGGGCAAA TCCTCCAAAA GGGAAAGGGA    3660

GGATTTGCTT AGAAGGATGG GGCTCCCAGT GACTACTTTT TGACTTCTGT TTGTCTTACG    3720

CTTCTCTCAG GGAAAAACAT GCAGTCCTCT AGTGTTTCAT GTACATTCTG TGGGGGGTGA    3780

ACACCTTGGT TCTGGTTAAA CAGCTGTACT TTTGATAGCT GTGCCAGGAA GGGTTAGGAC    3840
```

```
CAACTACAAA TTAATGTTGG TTGTGCAAAT GTAGTGTGTT TCCCTAACTT TCTGTTTTTC    3900

CTGAGAAAAA AAAATAAATC TTTTATTCAA ATAAAAAAAA AAAAAA                  3946
```

(2) INFORMATION FOR SEQ ID NO:2:

(i) SEQUENCE CHARACTERISTICS:
        (A) LENGTH: 350 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: mcl-1

(ix) FEATURE:
        (A) NAME/KEY: CDS
        (B) LOCATION: 1..3946
        (D) OTHER INFORMATION: /note= "When nucleotide 740 = C,
            amino acid 227 = A; when nucleotide 740 = T, amino
            acid 227 = V"

(ix) FEATURE:
        (A) NAME/KEY: Peptide
        (B) LOCATION: 1..350
        (D) OTHER INFORMATION: /note= "When nucleotide 740 = C,
            amino acid 227 = A; when nucleotide 740 = T, amino
            acid 227 = V."

(xi) SEQUENCE DESCRIPTION: SEQ ID NO:2:

```
Met Phe Gly Leu Lys Arg Asn Ala Val Ile Gly Leu Asn Leu Tyr Cys
1               5                   10                  15

Gly Gly Ala Gly Leu Gly Ala Gly Ser Gly Ala Thr Arg Pro Gly
            20                  25                  30

Gly Arg Leu Leu Ala Thr Glu Lys Glu Ala Ser Ala Arg Arg Glu Ile
        35                  40                  45

Gly Gly Gly Glu Ala Gly Ala Val Ile Gly Gly Ser Ala Gly Ala Ser
    50                  55                  60

Pro Pro Ser Thr Leu Thr Pro Asp Ser Arg Arg Val Ala Arg Pro Pro
65                  70                  75                  80

Pro Ile Gly Ala Glu Val Pro Asp Val Thr Ala Thr Pro Ala Arg Leu
                85                  90                  95

Leu Phe Phe Ala Pro Thr Arg Arg Ala Ala Pro Leu Glu Glu Met Glu
            100                 105                 110

Ala Pro Ala Ala Asp Ala Ile Met Ser Pro Glu Glu Leu Asp Gly
        115                 120                 125

Tyr Glu Pro Glu Pro Leu Gly Lys Arg Pro Ala Val Leu Pro Leu Leu
    130                 135                 140

Glu Leu Val Gly Glu Ser Gly Asn Asn Thr Ser Thr Asp Gly Ser Leu
145                 150                 155                 160

Pro Ser Thr Pro Pro Pro Ala Glu Glu Glu Asp Glu Leu Tyr Arg
                165                 170                 175

Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Val Phe Gln Gly Met Leu Arg Lys Leu Asp Ile Lys Asn Glu
225                 230                 235                 240
```

-continued

```
Asp Asp Val Lys Ser Leu Ser Arg Val Met Ile His Val Phe Ser Asp
            245                 250                 255
Gly Val Thr Asn Trp Gly Arg Ile Val Thr Leu Ile Ser Phe Gly Ala
            260                 265                 270
Phe Val Ala Lys His Leu Lys Thr Ile Asn Gln Glu Ser Cys Ile Glu
            275                 280                 285
Pro Leu Ala Glu Ser Ile Thr Asp Val Leu Val Arg Thr Lys Arg Asp
            290                 295                 300
Trp Leu Val Lys Gln Arg Gly Trp Asp Gly Phe Val Glu Phe His
305                 310                 315                 320
Val Glu Asp Leu Glu Gly Gly Ile Arg Asn Val Leu Leu Ala Phe Ala
            325                 330                 335
Gly Val Ala Gly Val Gly Ala Gly Leu Ala Tyr Leu Ile Arg
            340                 345                 350
```

(2) INFORMATION FOR SEQ ID NO:3:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: bcl-2alpha (ix) FEATURE:
        (A) NAME/KEY: Protein
        (B) LOCATION: 1..154

(xi) SEQUENCE DESCRIPTION: SEQ ID NO:3:

```
Leu Ser Pro Val Pro Pro Val Val His Leu Thr Leu Arg Gln Ala Gly
1               5                   10                  15
Asp Asp Phe Ser Arg Arg Tyr Arg Arg Asp Phe Ala Glu Met Ser Arg
            20                  25                  30
Gln Leu His Leu Thr Pro Phe Thr Ala Arg Gly Arg Phe Ala Thr Val
            35                  40                  45
Val Glu Glu Leu Phe Arg Asp Gly Val Asn Trp Gly Arg Ile Val Ala
            50                  55                  60
Phe Phe Glu Phe Gly Gly Val Met Cys Val Glu Ser Val Asn Arg Glu
65                  70                  75                  80
Met Ser Pro Leu Val Asp Asn Ile Ala Leu Trp Met Thr Glu Tyr Leu
            85                  90                  95
Asn Arg His Leu His Thr Trp Ile Gln Asp Asn Gly Gly Trp Asp Ala
            100                 105                 110
Phe Val Glu Leu Tyr Gly Pro Ser Met Arg Pro Leu Phe Asp Phe Ser
            115                 120                 125
Trp Leu Ser Leu Lys Thr Leu Leu Ser Leu Ala Leu Val Gly Ala Cys
            130                 135                 140
Ile Thr Leu Gly Ala Tyr Leu Gly His Lys
145                 150
```

(2) INFORMATION FOR SEQ ID NO:4:

(i) SEQUENCE CHARACTERISTICS:
        (A) LENGTH: 152 amino acids
        (B) TYPE: amino acid
        (C) STRANDEDNESS: single
        (D) TOPOLOGY: linear

```
    (ii) MOLECULE TYPE: protein (vii) IMMEDIATE SOURCE:
            (B) CLONE: BHRF-1

(ix) FEATURE:
            (A) NAME/KEY: Protein
            (B) LOCATION: 1..152

(xi) SEQUENCE DESCRIPTION: SEQ ID NO:4:

Leu Ser Pro Glu Asp Thr Val Val Leu Arg Tyr His Val Leu Leu Glu
1               5                   10                  15

Glu Ile Ile Glu Arg Asn Ser Glu Thr Phe Thr Glu Thr Trp Asn Arg
            20                  25                  30

Phe Ile Thr His Thr Glu His Val Asp Leu Asp Phe Asn Ser Val Phe
        35                  40                  45

Leu Glu Ile Phe His Arg Gly Asp Pro Ser Leu Gly Arg Ala Leu Ala
    50                  55                  60

Trp Met Ala Trp Cys Met His Ala Cys Arg Thr Leu Cys Cys Asn Gln
65                  70                  75                  80

Ser Thr Pro Tyr Tyr Val Val Asp Leu Ser Val Arg Gly Met Leu Glu
                85                  90                  95

Ala Ser Glu Gly Leu Asp Gly Trp Ile His Gln Gln Gly Gly Trp Ser
            100                 105                 110

Thr Leu Ile Glu Asp Asn Ile Pro Gly Ser Arg Arg Phe Ser Trp Thr
        115                 120                 125

Leu Phe Leu Ala Gly Leu Thr Leu Ser Leu Leu Val Ile Cys Ser Tyr
    130                 135                 140

Leu Phe Ile Ser Arg Gly Arg His
145                 150
```